US008569551B2

(12) United States Patent
Jevtic et al.

(10) Patent No.: US 8,569,551 B2
(45) Date of Patent: Oct. 29, 2013

(54) ALCOHOL PRODUCTION PROCESS INTEGRATING ACETIC ACID FEED STREAM COMPRISING WATER FROM CARBONYLATION PROCESS

(75) Inventors: Radmila Jevtic, Pasadena, TX (US); Victor J. Johnston, Houston, TX (US); Tianshu Pan, Houston, TX (US); Mark O. Scates, Houston, TX (US); Ronald David Shaver, Houston, TX (US); R. Jay Warner, Houston, TX (US); Heiko Weiner, Pasadena, TX (US); Josefina T. Chapman, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 225 days.

(21) Appl. No.: 13/094,580

(22) Filed: Apr. 26, 2011

(65) Prior Publication Data

US 2012/0059197 A1   Mar. 8, 2012

Related U.S. Application Data

(60) Provisional application No. 61/332,696, filed on May 7, 2010.

(51) Int. Cl.
*C07C 29/80* (2006.01)

(52) U.S. Cl.
USPC .......................................................... 568/885

(58) Field of Classification Search
USPC .......................................................... 568/885
See application file for complete search history.

(56) References Cited

U.S. PATENT DOCUMENTS

| | | | |
|---|---|---|---|
| 2,021,698 A | 11/1935 | Perkins | |
| 2,105,540 A | 1/1938 | Lazier | |
| 2,425,389 A | 8/1947 | Oxley | |
| 2,549,416 A | 4/1951 | Brooks | |
| 2,607,807 A | 8/1952 | Ford | |
| 2,702,783 A | 2/1955 | Harrison | |
| 2,744,939 A | 5/1956 | Kennel | |
| 2,801,209 A | 7/1957 | Muller | |
| 2,859,241 A | 11/1958 | Schnizer | |
| 2,882,244 A | 4/1959 | Milton | |
| 3,130,007 A | 4/1964 | Breck | |
| 3,478,112 A | 11/1969 | Adam | |
| 3,702,886 A | 11/1972 | Araguer | |
| 3,729,429 A | 4/1973 | Robson | |
| 3,953,524 A | 4/1976 | Steiner | |
| 4,052,467 A | 10/1977 | Mills | |
| 4,065,512 A | 12/1977 | Cares | |
| 4,228,307 A | 10/1980 | Zimmerschied | |
| 4,270,015 A | 5/1981 | Knifton | |
| 4,275,228 A | 6/1981 | Gruffaz | |
| 4,306,942 A | 12/1981 | Brush | |
| 4,317,918 A | 3/1982 | Takano | |
| 4,319,058 A | 3/1982 | Kulprathipanja | |
| 4,328,373 A | 5/1982 | Strojny | |
| 4,337,351 A | 6/1982 | Larkins, Jr. | |
| 4,379,028 A | 4/1983 | Berg | |
| 4,395,576 A | 7/1983 | Kwantes | |
| 4,398,039 A | 8/1983 | Pesa | |
| 4,399,305 A | 8/1983 | Schreck | |
| 4,421,939 A | 12/1983 | Kiff | |
| 4,426,541 A | 1/1984 | King | |
| 4,443,639 A | 4/1984 | Pesa | |
| 4,451,677 A | 5/1984 | Bradley | |
| 4,454,358 A | 6/1984 | Kummer | |
| 4,465,854 A | 8/1984 | Pond | |
| 4,471,136 A | 9/1984 | Larkins | |
| 4,480,115 A | 10/1984 | McGinnis | |
| 4,492,808 A | 1/1985 | Hagen | |
| 4,497,967 A | 2/1985 | Wan | |
| 4,517,391 A | 5/1985 | Schuster | |
| 4,521,630 A | 6/1985 | Wattimena | |
| 4,541,897 A | 9/1985 | Sommer | |
| 4,550,185 A | 10/1985 | Mabry | |
| 4,569,726 A | 2/1986 | Berg | |
| 4,581,473 A | 4/1986 | Polichnowski | |
| 4,592,806 A | 6/1986 | Ilgner et al. | |
| 4,613,700 A | 9/1986 | Maki | |
| 4,626,321 A | 12/1986 | Grethlein | |
| 4,626,604 A | 12/1986 | Hiles | |
| 4,678,543 A | 7/1987 | Houben | |
| 4,692,218 A | 9/1987 | Houben | |
| 4,762,817 A | 8/1988 | Logsdon | |
| 4,777,303 A | 10/1988 | Kitson | |
| 4,804,791 A | 2/1989 | Kitson | |

(Continued)

FOREIGN PATENT DOCUMENTS

| | | |
|---|---|---|
| CN | 1230458 | 10/1999 |
| CN | 102228831 | 11/2011 |

(Continued)

OTHER PUBLICATIONS

International Search Report and Written Opinion for PCT/US2011/035551 mailed Feb. 6, 2011 (12 pages).
Alcala, et al., (2005). Experimental and DFT studies of the conversion of ethanol and acetic acid on PtSn-based catalysts, Journal of Physical Chemistry, 109(6), 2074-2085.
Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.
Ammari, et al. An emergent catalytic material: Pt/ZnO catalyst for selective hydrogenation of crotonaldehyde, J. Catal. (2004), 221, p. 32-42.
Ammari, et al. Selective hydrogenation of crotonaldehyde on Pt/ZnCl2/SiO2 catalysts, J. Catal. (2005), 235, p. 1-9.

(Continued)

*Primary Examiner* — Sikarl Witherspoon

(57) ABSTRACT

In one embodiment, the invention is to a process for producing ethanol, comprising the step of providing from a distillation column in a carbonylation process a purified acetic acid stream comprising up to 25 wt. % water. The process further comprises the step of hydrogenating acetic acid of the purified acetic acid stream in the presence of a catalyst and under conditions effective to form a crude ethanol product comprising ethanol and water. Ethanol is recovered from the crude ethanol product.

29 Claims, 4 Drawing Sheets

(56) References Cited

U.S. PATENT DOCUMENTS

| | | |
|---|---|---|
| 4,826,795 A | 5/1989 | Kitson |
| 4,843,170 A | 6/1989 | Isshiki |
| 4,876,402 A | 10/1989 | Logsdon |
| 4,886,905 A | 12/1989 | Larkins, Jr. |
| 4,902,823 A | 2/1990 | Wunder |
| 4,943,354 A | 7/1990 | Osterburg et al. |
| 4,961,826 A | 10/1990 | Grethlein |
| 4,978,778 A | 12/1990 | Isshiki |
| 4,985,572 A | 1/1991 | Kitson |
| 4,990,655 A | 2/1991 | Kitson |
| 4,994,608 A | 2/1991 | Torrence |
| 5,001,259 A | 3/1991 | Smith |
| 5,004,845 A | 4/1991 | Bradley |
| 5,026,908 A | 6/1991 | Smith |
| 5,035,776 A | 7/1991 | Knapp |
| 5,061,671 A | 10/1991 | Kitson |
| 5,070,016 A | 12/1991 | Hallberg |
| 5,093,534 A | 3/1992 | Ludwig |
| 5,124,004 A | 6/1992 | Grethlein |
| 5,137,861 A | 8/1992 | Shih |
| 5,144,068 A | 9/1992 | Smith |
| 5,149,680 A | 9/1992 | Kitson |
| 5,155,084 A | 10/1992 | Horn |
| 5,185,308 A | 2/1993 | Bartley |
| 5,185,481 A | 2/1993 | Muto |
| 5,198,592 A | 3/1993 | van Beijnum |
| 5,215,902 A | 6/1993 | Tedder |
| 5,241,106 A | 8/1993 | Inoue |
| 5,243,095 A | 9/1993 | Roberts |
| 5,250,271 A | 10/1993 | Horizoe |
| 5,284,983 A | 2/1994 | Muto |
| 5,306,845 A | 4/1994 | Yokohama |
| 5,334,769 A | 8/1994 | Ferrero |
| 5,348,625 A | 9/1994 | Berg |
| 5,350,504 A | 9/1994 | Dessau |
| 5,415,741 A | 5/1995 | Berg |
| 5,426,246 A | 6/1995 | Nagahara |
| 5,437,770 A | 8/1995 | Berg |
| 5,445,716 A | 8/1995 | Berg |
| 5,449,440 A | 9/1995 | Rescalli |
| 5,475,144 A | 12/1995 | Watson |
| 5,476,827 A | 12/1995 | Ferrero |
| 5,480,665 A | 1/1996 | Smith |
| 5,488,185 A | 1/1996 | Ramachandran |
| 5,565,068 A | 10/1996 | Parker |
| RE35,377 E | 11/1996 | Steinberg |
| 5,585,523 A | 12/1996 | Weiguny |
| 5,599,976 A | 2/1997 | Scates |
| 5,663,430 A | 9/1997 | Morris |
| 5,674,800 A | 10/1997 | Abel |
| 5,691,267 A | 11/1997 | Nicolau |
| 5,696,284 A | 12/1997 | Baker |
| 5,719,315 A | 2/1998 | Tustin |
| 5,731,456 A | 3/1998 | Tustin |
| 5,762,765 A | 6/1998 | Berg |
| 5,767,307 A | 6/1998 | Ramprasad |
| 5,800,681 A | 9/1998 | Berg |
| 5,821,111 A | 10/1998 | Grady |
| 5,861,530 A | 1/1999 | Atkins |
| 5,877,347 A | 3/1999 | Ditzel |
| 5,877,348 A | 3/1999 | Ditzel |
| 5,883,295 A | 3/1999 | Sunley |
| 5,932,764 A | 8/1999 | Morris |
| 5,942,460 A | 8/1999 | Garland |
| 5,973,193 A | 10/1999 | Crane |
| 6,040,474 A | 3/2000 | Jobson |
| 6,049,008 A | 4/2000 | Roberts |
| 6,093,845 A | 7/2000 | van Acker |
| 6,114,571 A | 9/2000 | Abel |
| 6,121,498 A | 9/2000 | Tustin |
| 6,143,930 A | 11/2000 | Singh |
| 6,232,352 B1 | 5/2001 | Vidalin |
| 6,232,504 B1 | 5/2001 | Barteau |
| 6,326,515 B1 | 12/2001 | Clode |
| 6,375,807 B1 | 4/2002 | Nieuwoudt |
| 6,458,996 B1 | 10/2002 | Muskett |
| 6,462,231 B1 | 10/2002 | Yanagawa |
| 6,472,555 B2 | 10/2002 | Choudary |
| 6,476,261 B2 | 11/2002 | Ellis |
| 6,486,366 B1 | 11/2002 | Ostgard |
| 6,495,730 B1 | 12/2002 | Konishi |
| 6,509,180 B1 | 1/2003 | Verser |
| 6,509,290 B1 | 1/2003 | Vaughn |
| 6,603,038 B1 | 8/2003 | Hagemeyer |
| 6,627,770 B1 | 9/2003 | Cheung |
| 6,657,078 B2 | 12/2003 | Scates |
| 6,685,754 B2 | 2/2004 | Kindig |
| 6,693,213 B1 | 2/2004 | Kolena |
| 6,696,596 B1 | 2/2004 | Herzog |
| 6,768,021 B2 | 7/2004 | Horan |
| 6,812,372 B2 | 11/2004 | Janssen |
| 6,852,877 B1 | 2/2005 | Zeyss |
| 6,906,228 B2 | 6/2005 | Fischer |
| 6,927,048 B2 | 8/2005 | Verser |
| 7,005,541 B2 | 2/2006 | Cheung |
| 7,074,603 B2 | 7/2006 | Verser |
| 7,084,312 B1 | 8/2006 | Huber |
| 7,115,772 B2 | 10/2006 | Picard |
| 7,208,624 B2 | 4/2007 | Scates |
| 7,297,236 B1 | 11/2007 | Vander Griend |
| 7,351,559 B2 | 4/2008 | Verser |
| 7,425,657 B1 | 9/2008 | Elliott |
| 7,507,562 B2 | 3/2009 | Verser |
| 7,538,060 B2 | 5/2009 | Barnicki |
| 7,553,397 B1 | 6/2009 | Colley |
| 7,572,353 B1 | 8/2009 | Vander Griend |
| 7,601,865 B2 | 10/2009 | Verser |
| 7,608,744 B1 | 10/2009 | Johnston |
| 7,682,812 B2 | 3/2010 | Verser |
| 7,700,814 B2 | 4/2010 | Garton |
| 7,718,039 B2 | 5/2010 | Dirkzwager |
| 7,732,173 B2 | 6/2010 | Mairal |
| 7,744,727 B2 | 6/2010 | Blum et al. |
| 7,755,727 B2 | 7/2010 | Harada |
| 7,834,223 B2 | 11/2010 | Atkins |
| 7,842,844 B2 | 11/2010 | Atkins |
| 7,863,489 B2 | 1/2011 | Johnston |
| 7,884,253 B2 | 2/2011 | Stites |
| 7,888,082 B2 | 2/2011 | Verser |
| 2003/0013908 A1 | 1/2003 | Horan |
| 2003/0077771 A1 | 4/2003 | Verser |
| 2003/0104587 A1 | 6/2003 | Verser |
| 2003/0114719 A1 | 6/2003 | Fischer |
| 2004/0195084 A1 | 10/2004 | Hetherington |
| 2006/0019360 A1 | 1/2006 | Verser |
| 2006/0106246 A1 | 5/2006 | Warner |
| 2006/0127999 A1 | 6/2006 | Verser |
| 2007/0031954 A1 | 2/2007 | Mairal |
| 2007/0270511 A1 | 11/2007 | Melnichuk |
| 2008/0135396 A1 | 6/2008 | Blum |
| 2008/0193989 A1 | 8/2008 | Verser |
| 2008/0207953 A1 | 8/2008 | Houssin |
| 2009/0005588 A1 | 1/2009 | Hassan |
| 2009/0014313 A1 | 1/2009 | Lee |
| 2009/0023192 A1 | 1/2009 | Verser |
| 2009/0069609 A1 | 3/2009 | Kharas |
| 2009/0081749 A1 | 3/2009 | Verser |
| 2009/0166172 A1 | 7/2009 | Casey |
| 2009/0221725 A1 | 9/2009 | Chornet |
| 2009/0274880 A1 | 11/2009 | Iwasaka |
| 2009/0281354 A1 | 11/2009 | Mariansky |
| 2009/0299092 A1 | 12/2009 | Beavis |
| 2009/0318573 A1 | 12/2009 | Stites |
| 2009/0326080 A1 | 12/2009 | Chornet |
| 2010/0016454 A1 | 1/2010 | Gracey |
| 2010/0029980 A1 | 2/2010 | Johnston |
| 2010/0029993 A1 | 2/2010 | Johnston |
| 2010/0029995 A1 | 2/2010 | Johnston |
| 2010/0030001 A1 | 2/2010 | Johnston |
| 2010/0030002 A1 | 2/2010 | Johnston |
| 2010/0069514 A1 | 3/2010 | Gracey |
| 2010/0069515 A1 | 3/2010 | Tirtowidjojo |
| 2010/0113843 A1 | 5/2010 | Lee |
| 2010/0121114 A1 | 5/2010 | Weiner |

(56) References Cited

U.S. PATENT DOCUMENTS

| | | |
|---|---|---|
| 2010/0168466 A1 | 7/2010 | Johnston |
| 2010/0185021 A1 | 7/2010 | Ross |
| 2010/0197485 A1 | 8/2010 | Johnston |
| 2010/0197959 A1 | 8/2010 | Johnston |
| 2010/0197985 A1 | 8/2010 | Johnston |
| 2011/0004033 A1 | 1/2011 | Johnston |
| 2011/0046421 A1 | 2/2011 | Daniel |
| 2011/0082322 A1 | 4/2011 | Jevtic |
| 2011/0190548 A1 | 8/2011 | Jevtic |
| 2011/0224462 A1 | 9/2011 | Ditzel et al. |
| 2011/0275861 A1 | 11/2011 | Johnston |

FOREIGN PATENT DOCUMENTS

| | | |
|---|---|---|
| CN | 102229520 | 11/2011 |
| EP | 0056488 | 7/1982 |
| EP | 0104197 | 4/1984 |
| EP | 0120269 | 10/1984 |
| EP | 0137749 | 4/1985 |
| EP | 0167300 | 1/1986 |
| EP | 0175558 | 3/1986 |
| EP | 0192587 | 8/1986 |
| EP | 0234508 | 9/1987 |
| EP | 0285420 | 10/1988 |
| EP | 0330853 | 8/1989 |
| EP | 0372847 | 6/1990 |
| EP | 0400904 | 12/1990 |
| EP | 0198682 | 3/1991 |
| EP | 0539274 | 4/1993 |
| EP | 0285786 | 5/1993 |
| EP | 0953560 | 11/1999 |
| EP | 0990638 | 4/2000 |
| EP | 1277826 | 1/2003 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| GB | 1168785 | 10/1969 |
| GB | 1559540 | 1/1980 |
| GB | 2136704 | 9/1984 |
| JP | 06116182 | 4/1994 |
| JP | 10306047 | 11/1998 |
| JP | 2001046874 | 2/2001 |
| JP | 2001157841 | 6/2001 |
| WO | 8303409 | 10/1983 |
| WO | 9908791 | 4/1999 |
| WO | 03040037 A1 | 5/2003 |
| WO | 2007003897 | 1/2007 |
| WO | 2008135192 | 11/2008 |
| WO | 2009063176 | 5/2009 |
| WO | 2009105860 | 9/2009 |
| WO | 2010014148 | 2/2010 |
| WO | 2010014151 | 2/2010 |
| WO | 2010014153 | 2/2010 |
| WO | 2010055285 | 5/2010 |
| WO | 2011053365 | 5/2011 |

OTHER PUBLICATIONS

Consonni, et al. High Performances of Pt/ZnO Catalysts in Selective Hydrogenation of Crotonaldehyde, J. Catal. (1999), 1888, p. 165-175.

Djerboua, et al. On the performance of a highly loadedCO/SiO2 catalyst in the gas phase hydrogenation of crotonaldehyde thermal treatments—catalyst structure-selectivity relationship, Applied Catalysis A: General (2005), 282, p. 123-133.

English lanaguage abstract for EP 0539274 A1, Apr. 28, 1993.
English language abstract for EP 0 137 749 A2, Apr. 17, 1985.
English language abstract for EP 0 192 587 A1, Aug. 27, 1986.
English language abstract for EP 0 330 853 A2, Sep. 6, 1989.
English language abstract for EP 0 539 274 A1, Apr. 28, 1993.
English language abstract for JP 10306047 A, Nov. 17, 1998.
English language abstract for JP 2001-046874 A, Feb. 20, 2001.
English language abstract for JP 2001-157841 A, Jun. 12, 2001.
Gursahani et al., Reaction kinetics measurements and analysis of reaction pathways for conversions of acetic acid, ethanol, and ethyl acetate over silica-supported Pt, Applied Catalysis A: General 222 (2001) 369-392.
International Search Report and Written Opinion for PCT/US2009/004187 mailed Mar. 24, 2010 (10 pages).
International Search Report and Written Opinion for PCT/US2009/004195 mailed Mar. 26, 2010 (12 pages).
International Search Report and Written Opinion for PCT/US2011/023331 mailed Aug. 11, 2011.
Invition to Pay Additional Fees and Partial Search Report for PCT/US2011/023331 mailed May 4, 2011.
Liberkova and Tourounde, "Performance of Pt/SnO2 catalyst in the gas phase hydrogenation of crotonaldehyde," J. Mol. Catal. A: Chemical (2002), 180, p. 221-230.
Michael Gauβ, et al., Applied Homogeneous Catalysis with Organometallic Compounds: A Comprehensive Handbook in Volume Two, Chapter 2.1, p. 27-200, (1st ed., 1996).
Nitta, et al. Selective hydrogenation of a-unsaturated aldehydes on cobalt—silica catalysts obtained from cobalt chrysotile, Applied Catal. (1989), 56, p. 9-22.
Ordonez et al., The role of metal and support sites on the hydrogenation of acetic acid on Ru-based catalysts, 21st NAM San Francisco, CA, Jun. 10, 2009.
Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
Pestman et al., (1997). Reactions of Carboxylic Acids on Oxides, Journal of Catalysis 168, 255-264.
Pestman et al., (1998). Identification of the Active Sites in the Selective Hydrogenation of Acetic Acid to Acetaldehyde on Iron Oxide Catalysts, Journal of Catalysis, 174, 142-152.
Pestman et al., The formation of ketones and aldehydes from carboxylic acids, structure-activity relationship for two competitive reactions, Journal of Molecular Catalysis A: Chemical 103 Jun. 14, 1995, 175-180.
Proc. Roy Soc. A314, pp. 473-498 (1970).
Rachmady, Acetic Acid Reduction by H2 on Bimetallic Pt Fe Catalysts, Journal of Catalysis 209, 87-98 (Apr. 1, 2002), Elsevier Science (USA).
Rodrigues and Bueno Co/SiO2 catalysts for selective hydrogenation of crotonaldehyde: III. Promoting effect of zinc, Applied Catalysis A: General (2004), 257, p. 210-211.
Santori et al. (2000). Hydrogenation of carbonylic compounds on Pt/SiO2 catalysts modified with SnBu4, Studies in Surface Science and Catalysis, 130, 2063-2068.
ZeaChem, Inc., Technology Overview, Lakewood, Colorado www.zeachem.com, 2008.
Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.
Subramani et al., "A Review of Recent Literature to Search for an Efficient Catalytic Process for the Conversion of Syngas to Ethanol," Energy & Fuels, 2008, vol. 22, pp. 814-839.
Hilmen, Separation of Azeotropic Mixtures: Tools for Analysis and Studies on Batch Distillation Operation (Nov. 2000) p. 17-20.
English language abstract for JP 6-116182 A, Jun. 14, 1993.
International Preliminary Report on Patentability for PCT/US2011/035551 mailed Aug. 28, 2012.

ALCOHOL PRODUCTION PROCESS INTEGRATING ACETIC ACID FEED STREAM COMPRISING WATER FROM CARBONYLATION PROCESS

CROSS REFERENCE TO RELATED APPLICATIONS

This application claims priority to U.S. Provisional App. No. 61/332,696, filed on May 7, 2010, the entire contents and disclosures of which is incorporated herein by reference.

FIELD OF THE INVENTION

The present invention relates generally to alcohol production processes and, in particular, to ethanol production processes that integrate acetic acid feed streams from a carbonylation process. These acetic acid feed streams may comprise water.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are often formed with ethanol or are formed in side reactions. For example, during hydrogenation, esters are produced that together with ethanol and/or water form azeotropes, which are difficult to separate. These impurities may limit the production of ethanol and may require expensive and complex purification trains to separate the impurities from the ethanol. Also, the hydrogenation of acetic acid typically yields ethanol and water along with small amounts of side reaction-generated impurities and/or by-products. At maximum theoretical conversion and selectivity, the crude ethanol product would comprise approximately 72 wt. % ethanol and 28 wt. % water. In order to form purified ethanol, much of the co-produced water must be removed from the crude ethanol composition. In addition, when conversion is incomplete, unreacted acid may remain in the crude ethanol product. It is typically desirable to remove this residual acetic acid from the crude ethanol product to yield purified ethanol.

Some processes for integrating acetic acid production and hydrogenation have been proposed in literature. Generally, acetic acid production produces glacial acetic acid that has less than 1500 wppm water.

For example, U.S. Pat. No. 7,884,253 discloses methods and apparatuses for selectively producing ethanol from syngas. The syngas is derived from cellulosic biomass (or other sources) and can be catalytically converted into methanol, which in turn can be catalytically converted into acetic acid or acetates. The ethanoic acid product may be removed from the reactor by withdrawing liquid reaction composition and separating the ethanoic acid product by one or more flash and/or fractional distillation stages from the other components of the liquid reaction composition such as iridium catalyst, ruthenium and/or osmium and/or indium promoter, methyl iodide, water and unconsumed reactants which may be recycled to the reactor to maintain their concentrations in the liquid reaction composition.

EP2060553 discloses a process for the conversion of a carbonaceous feedstock to ethanol wherein the carbonaceous feedstock is first converted to ethanoic acid, which is then hydrogenated and converted into ethanol.

U.S. Pat. No. 4,497,967 discloses an integrated process for the preparation of ethanol from methanol, carbon monoxide and hydrogen feedstock. The process esterifies an acetic anhydride intermediate to form ethyl acetate and/or ethanol.

U.S. Pat. No. 7,351,559 discloses a process for producing ethanol including a combination of biochemical and synthetic conversions results in high yield ethanol production with concurrent production of high value co-products. An acetic acid intermediate is produced from carbohydrates, such as corn, using enzymatic milling and fermentation steps, followed by conversion of the acetic acid into ethanol using esterification and hydrogenation reactions.

As such, the need remains for improvements in the integration of acetic acid production and ethanol production.

SUMMARY OF THE INVENTION

In a first embodiment, the present invention is directed to a process for producing ethanol, comprising the step of providing from a distillation column in a carbonylation process a purified acetic acid stream comprising up to 25 wt. % water. The process further comprises the step of hydrogenating acetic acid of the purified acetic acid stream in the presence of a catalyst and under conditions effective to form a crude ethanol product comprising ethanol and water. The ethanol may then be recovered from the crude ethanol product.

In a second embodiment, a purified acetic acid sidedraw is withdrawn from a light ends column of a carbonylation process to provide the purified acetic acid stream. In another embodiment, the selection of the location from which the sidedraw is withdrawn may be based on a desired water content of the sidedraw.

BRIEF DESCRIPTION OF DRAWINGS

The invention is described in detail below with reference to the appended drawings, wherein like numerals designate similar parts.

DETAILED DESCRIPTION OF THE INVENTION

Figure 1:
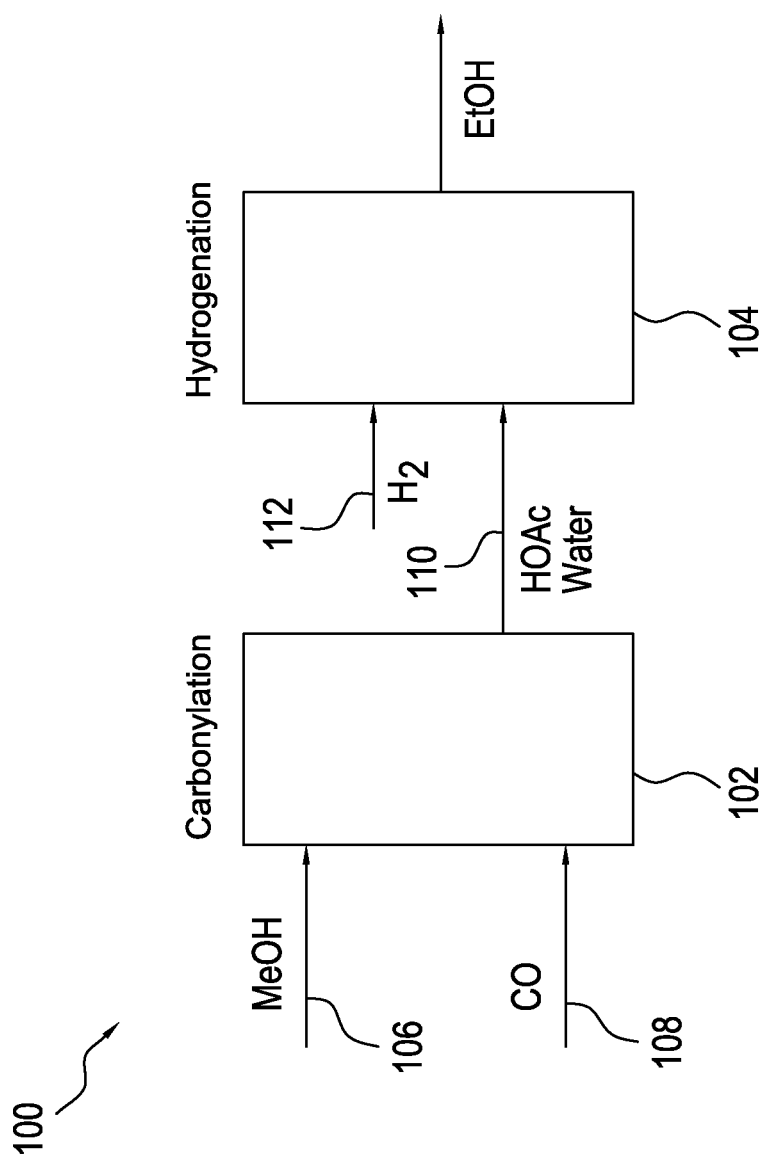
FIG. 1 is a diagram of an acetic acid and ethanol integrated production process in accordance with one embodiment of the present invention.

The present invention relates to processes for recovering ethanol produced by hydrogenating acetic acid of an acetic acid feed stream in the presence of a catalyst. The acetic acid feed stream may comprise acetic acid and water. The hydrogenation of the acetic acid forms a crude ethanol product comprising ethanol and water, generally in equal molar ratios. Including water in the acetic acid feed stream would be expected to be detrimental to ethanol production because water is a by-product of the reaction and is not converted during hydrogenation. However, it has now surprisingly and unexpectedly been found that feeding acetic acid and water in combination to a hydrogenation reactor does not substantially affect the conversion of acetic acid to ethanol and advantageously increases the efficiency of recovering ethanol from the resulting crude ethanol product. In one embodiment, feeding acetic acid and water in combination to the hydrogenation reactor may allow for more efficient ethanol separation requiring less energy.

In one embodiment, the acetic acid feed stream comprises water in amounts of up to 25 wt. %, e.g., up to 20 wt. % water, or up to 10 wt. % water. In terms of ranges the acetic acid feed stream may comprise from 0.15 wt. % to 25 wt. % water, e.g., from 0.2 wt. % to 20 wt. %, from 0.5 to 15 wt. %, or from 4 wt. % to 10. wt. %. In one embodiment, the acetic acid feed stream that is provided to the ethanol production process comprises water in an amount of at least 1500 wppm, e.g., at least 2500 wppm, at least 5000 wppm, or at least 1 wt. %. The remaining portion of the acetic acid feed stream preferably comprises acetic acid and hydrogen, preferably in a molar ratio of hydrogen to acetic acid from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1. In some embodiments, the acetic acid feed stream may also comprise other carboxylic acids and anhydrides, as well as optionally acetaldehyde and/or acetone. In particular, the acetic acid feed stream may comprise methyl acetate and/or propanoic acid. These other compounds may also be hydrogenated in the processes of the present invention.

Surprisingly and unexpectedly, the presence of water in amounts of up to 25 wt. % does not significantly reduce acetic acid conversion or selectivity to ethanol. For purposes of the present invention, the term "conversion" refers to the amount of acetic acid in the feed that is converted to a compound other than acetic acid. Conversion is expressed as a mole percentage based on acetic acid in the feed. Selectivity is expressed as a mole percent based on converted acetic acid. It should be understood that each compound converted from acetic acid has an independent selectivity and that selectivity is independent of conversion. Although conversion and selectivity to ethanol may vary depending on the reaction conditions and catalyst, the presence of water does not result in significant variations to the acetic acid conversion or selectivity to ethanol.

In recovering ethanol, the crude ethanol product would be expected to comprise more water than would be produced from hydrogenating glacial acetic acid. The crude ethanol product preferably comprises from 5 to 70 wt. % ethanol, e.g., from 30 to 70 wt. % ethanol or from 45 to 70 wt. % ethanol, and from 5 to 60 wt. % water, e.g., from 15 to 60 wt. % water or from 20 to 60 wt. % water. Advantageously, having more water initially in the crude ethanol product may reduce the requirement to boil over water in the initial distillation column while recovering ethanol. Generally, the amount of water in the distillate from the initial distillation column may be closer to the azeotropic amount of water that forms with the ethanol/water azeotrope, preferably less than 20 wt. %, or less than 12 wt. %. Further separation of ethanol from the distillate may also be improved because of the reduced amounts of water. In one embodiment, the weight ratio of water in the residue to the water in the distillate is greater than 2:1, e.g., greater than 4:1 or greater than 6:1. In some embodiments, particularly at higher conversions, the residue stream from the first distillation column may have a minor amount of acetic acid, e.g., less than 10 wt. %, or less than 5 wt. %, which allows the residue stream to be treated in a weak acid recovery system or sent to a reactive distillation column to convert the acid to esters.

Carbonylation

In one embodiment, the acetic acid may be produced from a carbonylation process. Conventional carbonylation processes yield a glacial acetic acid product comprising less than 1500 wppm water, e.g., less than 500 wppm, or less than 100 wppm. This product typically requires an energy intensive dehydrating step to achieve these low water levels. Embodiments of the present invention may, beneficially, eliminate the dehydrating step and/or allow the carbonylation process to run at reduced operating conditions, e.g., lower energy requirements. Advantageously the present invention achieves an improvement in integration by allowing more water to be present in the acetic acid.

FIG. 1 is a diagram of an integrated process 100 in accordance with the present invention. Process 100 comprises carbonylation system 102 and hydrogenation system 104. Carbonylation system 102 receives methanol feed 106 and carbon monoxide feed 108. The methanol and the carbon monoxide are reacted in carbonylation zone 102 to form an crude product comprising acetic acid and water. A flasher may be used to remove residual catalyst from the crude product. Carbonylation system 102, in some embodiments, further comprises a purification train comprising one or more distillation column (not shown in FIG. 1) to separate crude product into an acetic acid product stream 110 comprising from 0.15 wt. % to 25 wt. % water.

Acetic acid product stream 110 is fed, more preferably directly fed, to hydrogenation system 104. Water is already present in acetic acid product stream 110 and generally it is not necessary to further add water, e.g., to co-feed water. Thus, the water fed to hydrogenation system 104 is preferably provided by acetic acid product stream 110. Hydrogenation system 104 also receives hydrogen feed 112. In hydrogenation system 104, the acetic acid in acetic acid product stream is hydrogenated to form a crude ethanol product comprising ethanol and other compounds such as water, ethyl acetate, and unreacted acetic acid. Hydrogenation system 104 further comprises one or more separation units, e.g. distillation columns, for recovering ethanol from the crude ethanol product. An ethanol product stream 114 may be recovered from hydrogenation system 104.

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. For purposes of the present invention, acetic acid may be produced via methanol carbonylation as described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507, 562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884, 253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as syngas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

Although carbonylation may be a preferred acetic acid production method, other suitable methods may be employed. In a preferred embodiment that employs carbonylation, as shown in FIG. 1, carbonylation system 102 preferably comprises a reaction zone, which includes a reactor, a flasher and optionally a reactor recovery unit. In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt.

Suitable catalysts include Group VIII catalysts, e.g., rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volume*, Chapter 2.1, p. 27-200, (1$^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in U.S. Pat. Nos. 5,942,460; 5,932,764; 5,883,295; 5,877,348; 5,877,347; and 5,696,284, which are hereby incorporated by reference.

A halogen co-catalyst/promoter is generally used in combination with the Group VIII metal catalyst component. Methyl iodide is a preferred halogen promoter. Preferably, the concentration of halogen promoter in the reaction medium ranges from 1 wt. % to 50 wt. %, and preferably from 2 wt. % to 30 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in the reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa Acetic acid is typically manufactured in a liquid phase reaction at a temperature from about 150° C. to about 200° C. and a total pressure of from about 2 to about 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Water may be formed in situ in the reaction medium, for example, by the esterification reaction between methanol reactant and acetic acid product. In some embodiments, water is introduced to reactor together with or separately from other components of the reaction medium. Water may be separated from the other components of reaction product withdrawn from reactor and may be recycled in controlled amounts to maintain the required concentration of water in the reaction medium. Preferably, the concentration of water maintained in the reaction medium ranges from 0.1 wt. % to 16 wt. %, e.g., from 1 wt. % to 14 wt. %, or from 1 wt. % to 3 wt. % of the total weight of the reaction product.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt % to 30 wt. %, e.g., from 1 wt. % to 25 wt. %, or from 2 wt. % to 20 wt. %; and the lithium iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

Hydrogenation of Acetic Acid

The carbonylation system may be integrated with an acetic acid hydrogenation process to produce ethanol with the following hydrogenation reaction conditions and catalysts.

The acetic acid, along with water, may be vaporized at the reaction temperature, following which the vaporized acetic acid can be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol according to one embodiment of the invention may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 to 50,000 $hr^{-1}$, e.g., from 500 $hr^{-1}$ to 30,000 from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. Most preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another, or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from both the first and second metals. In preferred embodiments, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal is preferably from 0.05 to 4 wt. %, e.g., from 0.1 to 3 wt. %, or from 0.1 to 2 wt. %.

In addition to one or more metals, in some embodiments of the present invention, the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include siliceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. The basic support modifier may be selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 $m^2/g$; median pore diameter of about 12 nm; average pore volume of about 1.0 $cm^3/g$ as measured by mercury intrusion porosimetry; and packing density of about 0.352 $g/cm^3$ (22 $lb/ft^3$).

Another preferred silica support material is KA-160 silica spheres from Süd-Chemie having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 60 wt. % water. In some exemplary embodiments, the crude ethanol product comprises ethanol in an amount from 5 to 70 wt. %, e.g., from 30 to 70 wt. %, or from 45 to 70 wt. %, based on the total weight of the crude ethanol product. Preferably, the crude ethanol product contains at least 10 wt. % ethanol, at least 15 wt. % ethanol or at least 20 wt. % ethanol. As indicated above, water will generally be present in amounts greater than expected from hydrogenating glacial acetic acid. The crude ethanol product may contain, for example, from 5 to 60 wt. % water, e.g., from 15 to 60 wt. % water or from 20 to 60 wt. % water.

The crude ethanol product may also further comprise unreacted acetic acid, depending on conversion, for example, in an amount of less than 90 wt. %, e.g., less than 80 wt. % or less than 70 wt. %. In terms of ranges, the unreacted acetic acid optionally is present in the crude ethanol product in an amount from 0 to 90 wt. %, e.g., from 1 to 80 wt. %, from 2 to 70 wt. %, or from 5 to 70 wt. %. Ethyl acetate may also be produced during the hydrogenation of acetic acid, or through side reactions and may be present, for example, in amounts ranging from 0 to 20 wt. %, e.g., from 0 to 15 wt. %, from 1 to 12 wt. % or from 3 to 10 wt %. In addition, acetaldehyde may be produced through side reactions, and may be present, for example, in amounts ranging from 0 to 10 wt. %, e.g., from 0 to 3 wt. %, from 0.1 to 3 wt. % or from 0.2 to 2 wt. %. Other components, such as, for example, alcohols, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be collectively present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT

| Component | Conc. (wt. %) | Conc. (wt. %) | Conc. (wt. %) | Conc. (wt. %) |
|---|---|---|---|---|
| Ethanol | 5 to 70 | 30 to 70 | 45 to 70 | 25 to 50 |
| Acetic Acid | 0 to 90 | 1 to 80 | 2 to 70 | 5 to 70 |
| Water | 5 to 60 | 15 to 60 | 20 to 60 | 20 to 40 |
| Ethyl Acetate | 0 to 35 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Integration Carbonylation and Hydrogenation

Figure 2:
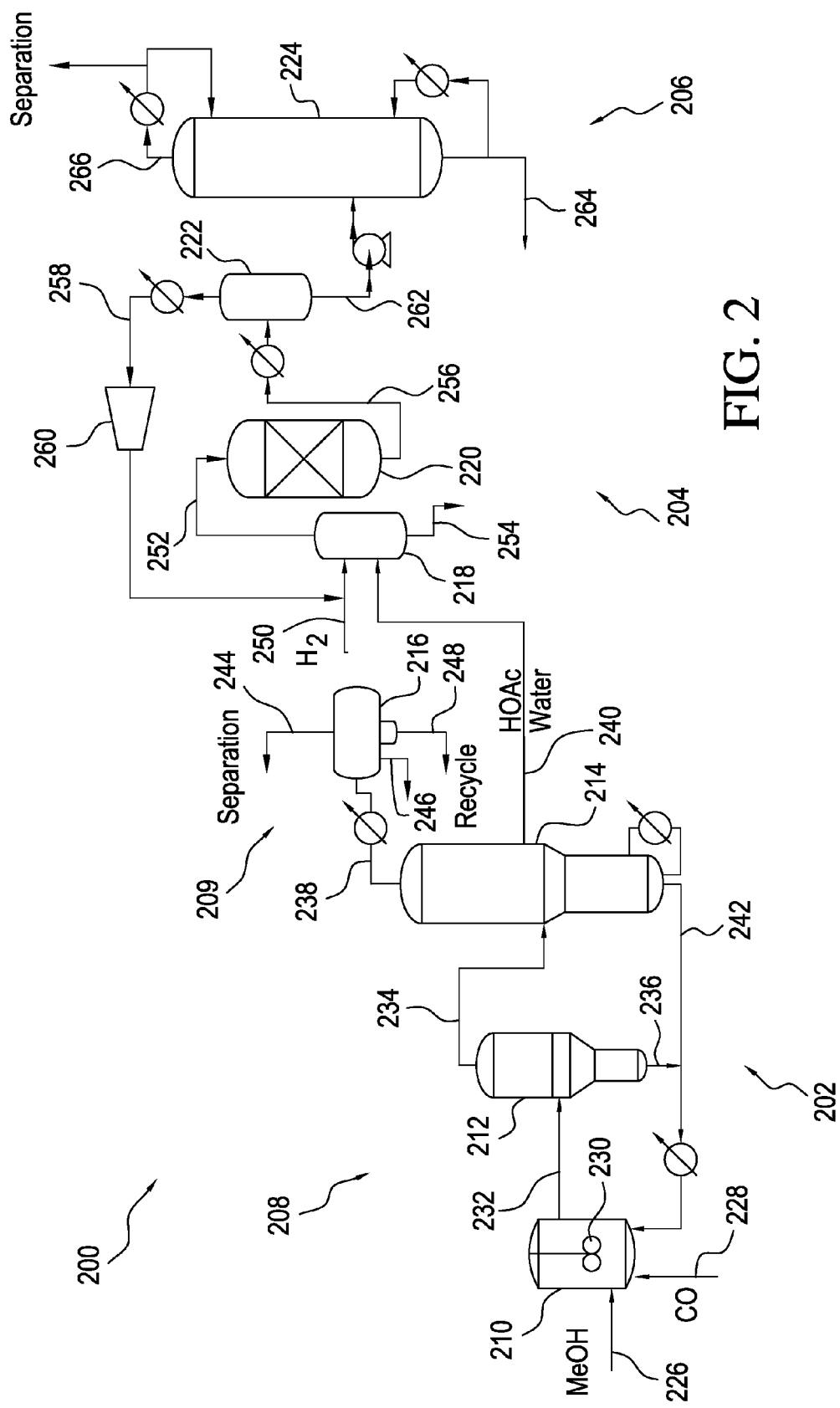
FIG. 2 is a schematic diagram of an exemplary integrated carbonylation and hydrogenation process in accordance with one embodiment of the present invention.
Figure 3:
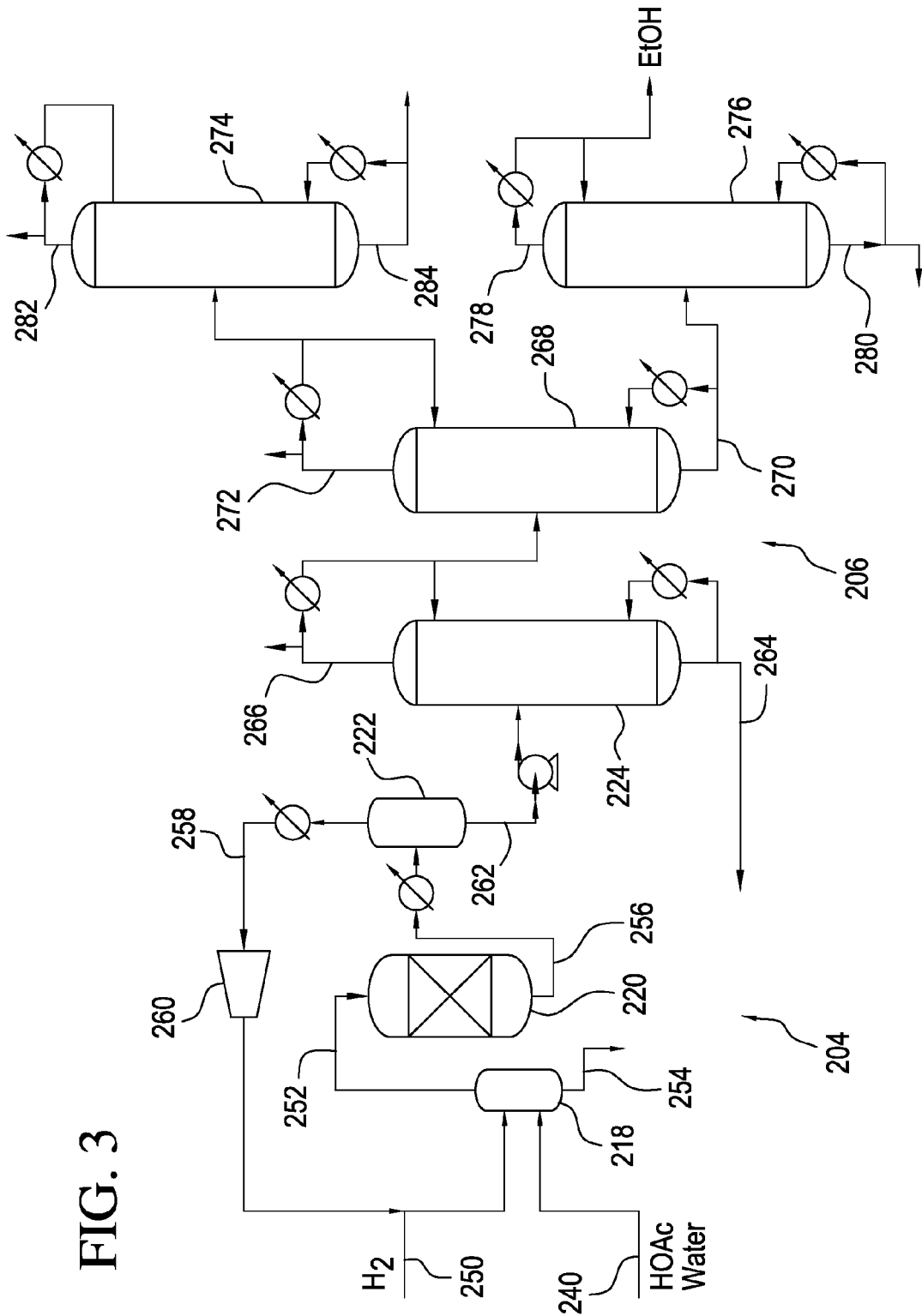
FIG. 3 is a schematic diagram of a hydrogenation zone in accordance with one embodiment of the present invention.

FIG. 2 shows exemplary integrated carbonylation and hydrogenation process 200, which comprises carbonylation system 202, hydrogenation zone 204, and hydrogenation separation zone 206. Carbonylation system 202 comprises 1) reaction zone 208, which comprises carbonylation reactor 210 and flasher 212, and 2) carbonylation separation zone 209, which comprises at least one distillation column, e.g., a light ends column or a drying column, 214, and phase separator, e.g., decanter, 216. Hydrogenation zone 204 comprises vaporizer 218 and hydrogenation reactor 220. Hydrogenation separation zone 206 comprises flasher 222 and column 224, also referred to as an "acid separation column." FIG. 3 is an exemplary hydrogenation zone 204 with a hydrogenation separation zone 206 having multiple columns.

In carbonylation system 202, methanol feed stream 226 comprises methanol and/or reactive derivatives thereof and carbon monoxide 228 are fed to a lower portion of carbonylation reactor 210. Suitable reactive derivatives of methanol include methyl acetate, dimethyl ether, methyl formate, and mixtures thereof. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range of from 0.5 wt. % to 70 wt. %, e.g., from 0.5 wt. % to 50 wt. %, from 1 wt. % to 35 wt. %, or from 1 wt. % to 20 wt. %.

Reactor 210 is preferably either a stirred vessel, e.g., CSTR, or bubble-column type vessel, with agitator 230 or without an agitator, within which the reaction medium is maintained, preferably automatically, at a predetermined level. This predetermined level may remain substantially constant during normal operation. Into reactor 210, methanol, carbon monoxide, and sufficient water may be continuously introduced as needed to maintain at least a finite concentration of water in the reaction medium. In one embodiment, carbon monoxide, e.g., in the gaseous state, is continuously introduced into reactor 210, desirably below agitator 230, which is used to stir the contents. The temperature of reactor 210 may be controlled, as indicated above. Carbon monoxide feed 228 is introduced at a rate sufficient to maintain the desired total reactor pressure.

The gaseous carbon monoxide feed is preferably thoroughly dispersed through the reaction medium by agitator 230. A gaseous purge is desirably vented via an off-gas line (not shown) from reactor 210 to prevent buildup of gaseous by-products, such as methane, carbon dioxide, and hydrogen, and to maintain a carbon monoxide partial pressure at a given total reactor pressure.

The crude acetic acid product is drawn off from the reactor 210 at a rate sufficient to maintain a constant level therein and is provided to flasher 212 via stream 232.

In flasher 212, the crude acetic acid product is separated in a flash separation step to obtain a volatile ("vapor") overhead stream 234 comprising acetic acid and a less volatile stream 236 comprising a catalyst-containing solution. The catalyst-containing solution comprises acetic acid containing the rhodium and the iodide salt along with lesser quantities of methyl acetate, methyl iodide, and water. The less volatile stream 236 preferably is recycled to reactor 210. Vapor overhead stream 234 also comprises methyl iodide, methyl acetate, water, and permanganate reducing compounds ("PRCs").

Overhead stream 234 from flasher 212 is directed to separation zone 209. Separation zone 209 comprises light ends column 214 and decanter 216. Separation zone 209 may also comprise additional units, e.g., a drying column, one or more columns for removing PRCs, heavy ends columns, extractors, etc.

In light ends column 214, stream 234 yields a low-boiling overhead vapor stream 238, a purified acetic acid stream that preferably is removed via a sidestream 240, and a high boiling residue stream 242. Purified acetic acid that is removed via sidestream 240 preferably is conveyed, e.g., directly, without removing substantially any water therefrom, to hydrogenation system 204. Thus, the present invention provides for production efficiencies by using an acetic acid stream having a higher water content than glacial acetic acid, which beneficially reduces or eliminates the need for water removal downstream from light ends column 214 in carbonylation system 202.

In one embodiment, column 214 may comprise trays having different concentrations of water. In these cases, the composition of a withdrawn sidedraw may vary throughout the column. As such, the withdrawal tray may be selected based on the amount of water that is desired, e.g., more than 0.5 wt %. In another embodiment, the configuration of the column may be varied to achieve a desired amount or concentration of water in a sidedraw. Thus, an acetic acid feed may be produced, e.g., withdrawn from a column, based on a desired water content. Accordingly, in one embodiment, the invention is to a process for producing ethanol comprising the step of withdrawing a purified acetic acid sidedraw from a light ends column in a carbonylation process, wherein a location from which the sidedraw is withdrawn is based on a water content of the sidedraw. The water content of the sidedraw may be from 0.15 wt. % to 25 wt. % water. The process further comprises the steps of hydrogenating acetic acid of the purified acetic acid stream in the presence of a catalyst under conditions effective to form a crude ethanol product comprising ethanol and water; and recovering ethanol from the crude ethanol product.

In another embodiment, the separation zone 209 comprises a second column, such as a drying column (not shown). A portion of the crude acetic acid stream 240 may be directed to the second column to separate some of the water from sidedraw 240 as well as other components such as esters and halogens. In these cases, the drying column may yield an acetic acid residue comprising acetic acid and from 0.15 wt. % to 25 wt. % water. The acetic acid residue exiting the second column may be fed to hydrogenation system 204 in accordance with the present invention.

The purified acetic acid stream, in some embodiments, comprises methyl acetate, e.g., in an amount ranging from 0.01 wt. % to 10 wt. % or from 0.1 wt. % to 5 wt. %. This methyl acetate, in preferred embodiments, may be reduced to form methanol and/or ethanol. In addition to acetic acid, water, and methyl acetate, the purified acetic acid stream may comprise halogens, e.g., methyl iodide, which may be removed from the purified acetic acid stream.

Returning to column 214, low-boiling overhead vapor stream 238 is preferably condensed and directed to an overhead phase separation unit, as shown by overhead receiver decanter 216. Conditions are desirably maintained in the process such that low-boiling overhead vapor stream 238, once in decanter 216, will separate into a light phase and a heavy phase. Generally, low-boiling overhead vapor stream 238 is cooled to a temperature sufficient to condense and separate the condensable methyl iodide, methyl acetate, acetaldehyde and other carbonyl components, and water into two phases. A gaseous portion of stream 238 may include carbon monoxide, and other noncondensable gases such as methyl iodide, carbon dioxide, hydrogen, and the like and is vented from the decanter 216 via stream 244.

Condensed light phase 246 from decanter 216 preferably comprises water, acetic acid, and permanganate reducing compounds ("PRCs"), as well as quantities of methyl iodide and methyl acetate. Condensed heavy phase 248 from decanter 216 will generally comprise methyl iodide, methyl acetate, and PRCs. The condensed heavy liquid phase 248, in some embodiments, be recirculated, either directly or indirectly, to reactor 210. For example, a portion of condensed heavy liquid phase 248 can be recycled to reactor 210, with a slip stream (not shown), generally a small amount, e.g., from 5 to 40 vol. %, or from 5 to 20 vol. %, of the heavy liquid phase being directed to a PRC removal system. This slip stream of heavy liquid phase 248 may be treated individually or may be combined with condensed light liquid phase 246 for further distillation and extraction of carbonyl impurities in accordance with one embodiment of the present invention.

Acetic acid sidedraw 240 from distillation column 214 of carbonylation process 202 is preferably directed to hydrogenation system 204. In one embodiment, the purified acetic acid stream may be sidestream 240 from a light ends column 214.

In hydrogenation system 204, hydrogen feed line 250 and sidedraw 240 comprising acetic acid and water is fed to vaporizer 218. Vapor feed stream 252 is withdrawn and fed to hydrogenation reactor 220. In one embodiment, lines 250 and 240 may be combined and jointly fed to the vaporizer 218. The temperature of vapor feed stream 252 is preferably from 100° C. to 350° C., e.g., from 120° C. to 310° C. or from 150° C. to 300° C. Vapor feed stream 252 comprises from 0.15 wt. % to 25 wt. % water. Any feed that is not vaporized is removed from vaporizer 218 via stream 254, as shown in FIG. 2, and may be recycled thereto or discarded. In addition, although FIG. 2 shows line 252 being directed to the top of reactor 220, line 252 may be directed to the side, upper portion, or bottom of reactor 220. Further modifications and additional components to reaction zone 204 are described below.

Reactor 220 contains the catalyst that is used in the hydrogenation of the carboxylic acid, preferably acetic acid. During the hydrogenation process, a crude ethanol product is withdrawn, preferably continuously, from reactor 220 via line 256 and directed to separation zone 206.

Separation zone 206 comprises flasher 222, and first column 224. Further columns may be included as need to further separate and purify the crude ethanol product as shown in FIG. 3. The crude ethanol product may be condensed and fed to flasher 222, which, in turn, provides a vapor stream and a liquid stream. Flasher 222 may operate at a temperature of from 20° C. to 250° C., e.g., from 30° C. to 250° C. or from 60° C. to 200° C. The pressure of flasher 222 may be from 50 kPa to 2000 kPa, e.g., from 75 kPa to 1500 kPa or from 100 kPa to 1000 kPa.

The vapor stream exiting flasher 222 may comprise hydrogen and hydrocarbons, which may be purged and/or returned to reaction zone 204 via line 258. As shown in FIG. 2, the returned portion of the vapor stream passes through compressor 260 and is combined with the hydrogen feed and co-fed to vaporizer 218.

The liquid from flasher 222 is withdrawn and pumped as a feed composition via line 262 to the side of column 224, which may be referred to as the first column when multiple columns are used as shown in FIG. 3. Column 224 may also be referred to as an "acid separation column." The contents of line 262 typically will be substantially similar to the product obtained directly from the reactor 220, and may, in fact, also be characterized as a crude ethanol product. However, the feed composition in line 262 preferably has substantially no hydrogen, carbon dioxide, methane or ethane, which are removed by flasher 222. Exemplary compositions of line 262 are provided in Table 2. It should be understood that liquid line 262 may contain other components, not listed, such as additional components in the feed.

TABLE 2

FEED COMPOSITION

|  | Conc. (wt. %) | Conc. (wt. %) | Conc. (wt. %) |
| --- | --- | --- | --- |
| Ethanol | 5 to 70 | 30 to 70 | 25 to 50 |
| Acetic Acid | <90 | 1 to 80 | 2 to 70 |
| Water | 5 to 60 | 15 to 60 | 20 to 60 |
| Ethyl Acetate | <20 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Alcohols | <8 | <0.1 | <0.05 |
| Other Esters | <5 | <0.005 | <0.001 |
| Other Ethers | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 3 may include, but are not limited to, methanol, isopropanol, n-propanol, n-butanol or mixtures thereof. In one embodiment, the feed composition, e.g., line 262, may comprise propanol, e.g., isopropanol and/or n-propanol, in an amount from 0.001 to 0.1 wt. %, from 0.001 to 0.05 wt. % or from 0.001 to 0.03 wt. %. It should be understood that these other components may be carried through in any of the distillate or residue streams described herein.

Optionally, the crude ethanol product may pass through one or more membranes to separate hydrogen and/or other non-condensable gases. In other optional embodiments, the crude ethanol product may be fed directly to the acid separation column as a vapor feed and the non-condensable gases may be recovered from the overhead of the column.

When the content of acetic acid in line 262 is less than 5 wt. %, acid separation column 224 may be skipped and line 262 may be introduced directly to a second column, e.g., a "light ends column." In addition, column 224 may be operated to initially remove a substantial portion of water as the residue.

In the embodiment shown in FIG. 2, line 262 is introduced in the lower part of first column 224, e.g., lower half or lower third. Depending on the acetic acid conversion and operation of column 224, unreacted acetic acid, water, and other heavy components, if present, are removed from the composition in line 262 and are withdrawn, preferably continuously, as residue. In preferred embodiments, the presence of larger amounts of water in line 262 allows separation of a majority of water in line 262 along with substantially all the acetic acid in residue stream 264. All or a portion of residue stream 264 may be recycled to reaction zone 204 as necessary to maintain the water concentration amounts for the acetic acid feed stream. In addition, residue stream 264 may be separated into a water stream and an acetic acid stream, and either stream may be returned to reaction zone 204. In other embodiments, residue stream 264 may be a dilute acid stream that may be treated in a weak acid recovery system or sent to a reactive distillation column to convert the acid to esters.

First column 224 also forms an overhead distillate, which is withdrawn via stream 266, and which may be condensed and refluxed, for example, at a ratio of from 10:1 to 1:10, e.g., from 3:1 to 1:3 or from 1:2 to 2:1. As indicated above, a majority of the water is withdrawn in residue via line 264 as opposed to distillate via line 266 such that the weight ratio of water in line 264 to line 266 is greater than 2:1.

The columns shown in the FIGS. may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section and so on.

The associated condensers and liquid separation vessels that may be employed with each of the distillation columns may be of any conventional design and are simplified in FIGS. 2 and 3. As shown in FIGS. 2 and 3, heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in FIGS. 2 and 3, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatomic pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

When column 224 is operated under about 170 kPa, the temperature of the residue exiting in line 264 from column 224 preferably is from 90° C. to 130° C., e.g., from 95° C. to 120° C. or from 100° C. to 115° C. The temperature of the distillate exiting in line 266 from column 224 preferably is from 60° C. to 90° C., e.g., from 65° C. to 85° C. or from 70° C. to 80° C. In some embodiments, the pressure of first column 224 may range from 0.1 kPa to 510 kPa, e.g., from 1 kPa to 475 kPa or from 1 kPa to 375 kPa. Distillate and residue compositions for first column 224 for one exemplary embodiment of the present invention are provided in Table 3. In addition, for convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

FIRST COLUMN

|  | Conc. (wt. %) | Conc. (wt. %) | Conc. (wt. %) |
|---|---|---|---|
| Distillate |  |  |  |
| Ethanol | 20 to 90 | 30 to 85 | 50 to 85 |
| Water | 4 to 38 | 7 to 32 | 7 to 25 |
| Acetic Acid | <1 | 0.001 to 1 | 0.01 to 0.5 |
| Ethyl Acetate | <60 | 5 to 40 | 8 to 45 |
| Acetaldehyde | <10 | 0.001 to 5 | 0.01 to 4 |
| Acetal | <4.0 | <3.0 | <2.0 |
| Acetone | <0.05 | 0.001 to 0.03 | 0.01 to 0.025 |
| Residue |  |  |  |
| Acetic Acid | <90 | 1 to 50 | 2.5 to 40 |
| Water | 30 to 100 | 45 to 90 | 60 to 90 |
| Ethanol | <1 | <0.9 | <0.5 |

As indicated in Table 3, embodiments of the present invention allow a majority of the water to be withdrawn in residue line 264. In addition, the increased amount of water reduces the amount of acetic acid that may be carried over in distillate line 266. Preferably there is substantially no or very low amounts of acetic acid in distillate line 266. Reducing acetic acid in distillate line 266 may advantageously reduce the amount of acetic acid in the final ethanol product.

Some species, such as acetals, may decompose in column 224 such that very low amounts, or even no detectable amounts, of acetals remain in the distillate or residue. In addition, there may be an equilibrium reaction after the crude ethanol product exits reactor 220 in liquid feed 256. Depending on the concentration of acetic acid in the crude ethanol product, equilibrium may be driven toward formation of ethyl acetate. The reaction may be regulated using the residence time and/or temperature of liquid feed 256.

The distillate, e.g., overhead stream, of column 224 optionally is condensed and refluxed as shown in FIG. 2, preferably, at a reflux ratio of 1:5 to 10:1. The distillate in line 266 preferably comprises ethanol, ethyl acetate, and lower amounts of water. The separation of these species may be difficult, in some cases, due to the formation of binary and tertiary azeotropes.

In some embodiments, depending on acetic conversion and the amount of water withdrawn from column 244, distillate in line 266 may comprise a suitable ethanol product that requires no further processing.

In one embodiment, as shown in FIG. 3, the first distillate in line 266 is further processed to remove byproducts. First distillate in line 266 is directed to the second column 268, also referred to as a "light ends column," preferably in the top part of column 268, e.g., top half or top third. Second column 268 may be a tray column or packed column. In one embodiment, second column 268 is a tray column having from 5 to 70 trays, e.g., from 15 to 50 trays, or from 20 to 45 trays. As one example, when a 30 tray column is used in a column without water extraction, line 266 is introduced at tray 2.

In another embodiment, second column 268 may be an extractive distillation column. In such an embodiment, an extraction agent, such as water, may be added to second column 268. If the extraction agent comprises water, it may be obtained from an external source or from an internal return/recycle line from one or more of the other columns. Other suitable extractive agents that may be used include dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or combinations thereof.

In some embodiments, a portion of the water in first distillate 266 may be removed prior to second column 268, using one or more membranes, and/or adsorptions units.

Although the temperature and pressure of second column 268 may vary, when at about 20 kPa to 70 kPa, the temperature of the second residue exiting in line 270 from second column 268 preferably is from 30° C. to 75° C., e.g., from 35° C. to 70° C. or from 40° C. to 65° C. The temperature of the second distillate exiting in line 272 from second column 268 preferably is from 20° C. to 55° C., e.g., from 25° C. to 50° C. or from 30° C. to 45° C. Second column 268 may operate at a reduced pressure, near or at vacuum conditions, to further favor separation of ethyl acetate and ethanol. In other embodiments, the pressure of second column 268 may range from 0.1 kPa to 510 kPa, e.g., from 1 kPa to 475 kPa or from 1 kPa to 375 kPa. Exemplary distillate and residue compositions for second column 268 are provided in Table 4 below. It should be understood that the distillate and residue may also contain other components, not listed, such as additional components in the feed.

TABLE 4

SECOND COLUMN

|  | Conc. (wt. %) | Conc. (wt. %) | Conc. (wt. %) |
|---|---|---|---|
| Distillate |  |  |  |
| Ethyl Acetate | 5 to 90 | 10 to 80 | 15 to 75 |
| Acetaldehyde | <60 | 1 to 40 | 1 to 35 |
| Water | <45 | 0.001 to 40 | 0.01 to 35 |
| Ethanol | <20 | 0.01 to 10 | 0.1 to 5 |
| Residue |  |  |  |
| Water | 5 to 70 | 30 to 60 | 30 to 50 |
| Ethanol | 20 to 95 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the second residue to ethanol in the second distillate preferably is at least 3:1, e.g., at least 6:1, at least 8:1, at least 10:1 or at least 15:1. The weight ratio of ethyl acetate in the second residue to ethyl acetate in the second distillate preferably is less than 0.4:1, e.g., less than 0.2:1 or less than 0.1:1. In embodiments that use an extractive column with water as an extraction agent as the second column 268, the weight ratio of ethyl acetate in the second residue to ethyl acetate in the second distillate is less than 0.1:1.

Returning to the second distillate, which comprises ethyl acetate and/or acetaldehyde, the second distillate preferably is refluxed as shown in FIG. 3, for example, at a reflux ratio of from 1:30 to 30:1, e.g., from 1:5 to 5:1 or from 1:3 to 3:1. In some embodiments, the second distillate in line 272 or portion thereof may be returned reactor 220. For example, it may be advantageous to return a portion of second distillate 272 to reactor 220. In certain embodiments and as shown in FIG. 3, the second distillate may be fed to "acetaldehyde removal column" 274 to recover aldehyde, which may be recycled to the reactor 220. Acetaldehyde removal column 274 may also separate the second distillate 272 to yield a residue, which comprises ethyl acetate. In other embodiments, the second distillate may be hydrolyzed or fed to a hydrogenolysis reactor (not shown) to produce ethanol from ethyl acetate. In still other embodiments, the second distillate may be purged from system.

Optionally, when second distillate 272 comprises water, the water may be removed using one or more membranes, and/or adsorptions units. The removed water may be purged or retained in the system by adding the acetic acid feed stream.

The second residue 270 from the bottom of second column 268, which may comprise ethanol and water, may be further separated depending on the concentration of water. As shown in FIG. 1, second residue 270 is directed to a third column 276 to remove the water and thus yield an ethanol product. In some embodiments, the amount of water in second residue 270 may be sufficient for the particular use of the ethanol product, such as for industrial uses. For uses that require lower amounts of water, in particular fuels, the water may be removed using a distillation column, membrane, adsorption unit, or combination thereof.

As shown in FIG. 3, the second residue is fed via line 270 to third column 276, also referred to as a "product column." The second residue in line 270 is introduced in the lower part of third column 276, e.g., lower half or lower third. Third column 276 recovers ethanol, which preferably is substantially pure other than the azeotropic water content, as the distillate in line 278. The distillate of third column 276 preferably is refluxed as shown in FIG. 3, for example, at a reflux ratio of from 1:10 to 10:1, e.g., from 1:3 to 3:1 or from 1:2 to 2:1. The third residue in line 280, which preferably comprises primarily water, may be returned to reaction zone 204. In some embodiments, the third residue may be used an extractive agent or to hydrolyze an ethyl acetate stream. Third column 276 is preferably a tray column as described above and preferably operates at atmospheric pressure. The temperature of the third distillate exiting in line 280 from third column 276 preferably is from 60° C. to 110° C., e.g., from 70° C. to 100° C. or from 75° C. to 95° C. The temperature of the third residue exiting from third column 276 preferably is from 70° C. to 115° C., e.g., from 80° C. to 110° C. or from 85° C. to 105° C., when the column is operated at atmospheric pressure. Exemplary components of the distillate and residue compositions for third column 276 are provided in Table 5 below. It should be understood that the distillate and residue may also contain other components, not listed, such as components in the feed.

TABLE 5

THIRD COLUMN

| | Conc. (wt. %) | Conc. (wt. %) | Conc. (wt. %) |
|---|---|---|---|
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts of less 0.1 wt. %, based on the total weight of the third distillate composition, e.g., less than 0.05 wt. % or less than 0.02 wt. %. In one embodiment, one or more side streams may remove impurities from any of the columns 224, 268, 274, and/or 276 in the system. Preferably at least one side stream is used to remove impurities from the third column 276. The impurities may be purged and/or retained within the system.

The ethanol product is taken from the third distillate 278. Third distillate 278 may be further purified to form an anhydrous ethanol product stream, i.e., "finished anhydrous ethanol," using one or more additional separation systems, such as, for example, distillation columns (e.g., a finishing column), membranes, adsorption units, or molecular sieves. Anhydrous ethanol may be suitable for fuel applications.

Returning to second column 268, in another embodiment, as shown in FIG. 3, the second distillate is fed via line 272 to fourth column 274, also referred to as the "acetaldehyde removal column." In fourth column 274 the second distillate is separated into a fourth distillate, which comprises acetaldehyde, in line 282. The fourth distillate preferably is refluxed at a reflux ratio of from 1:20 to 20:1, e.g., from 1:15 to 15:1 or from 1:10 to 10:1, and a portion of the fourth distillate is returned to reaction zone 204. For example, the fourth distillate may be combined with the acetic acid feed, added to the vaporizer 218, or added directly to the reactor 220. In one embodiment, the fourth distillate is co-fed with the acetic acid to vaporizer 218 (not shown). Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown in the FIG. 3), the acetaldehyde may be collected and utilized, with or without further purification, to make useful products including but not limited to n-butanol, 1,3-butanediol, and/or crotonaldehyde and derivatives.

The fourth residue of fourth column 274 in line 284 primarily comprises ethyl acetate and water and is highly suitable for use as an ester feed stream. In one preferred embodiment, the acetaldehyde is removed from the second distillate in fourth column 274 such that no detectable amount of acetaldehyde is present in the residue of fourth column 274.

Fourth column 274 is preferably a tray column as described above and preferably operates above atmospheric pressure. In one embodiment, the pressure is from 120 kPa to 5,000 kPa, e.g., from 200 kPa to 4,500 kPa, or from 400 kPa to 3,000 kPa.

In a preferred embodiment the fourth column 274 may operate at a pressure that is higher than the pressure of the other columns.

The temperature of the fourth distillate exiting in line 284 from fourth column 274 preferably is from 60° C. to 110° C., e.g., from 70° C. to 100° C. or from 75° C. to 95° C. The temperature of the residue exiting from fourth column 274 preferably is from 70° C. to 115° C., e.g., from 80° C. to 110° C. or from 85° C. to 110° C. Exemplary components of the distillate and residue compositions for fourth column 274 are provided in Table 6 below. It should also be understood that the distillate and residue may also contain other components, not listed, such as components in the feed.

TABLE 6

FOURTH COLUMN

|  | Conc. (wt. %) | Conc. (wt. %) | Conc. (wt. %) |
|---|---|---|---|
| Distillate |  |  |  |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |
| Residue |  |  |  |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

The final ethanol product produced by the process of the present invention may be taken from the third distillate. The ethanol product may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit such as an adsorption unit, membrane, molecular sieve, or extractive distillation column. In such embodiments, the ethanol concentration of the ethanol product may be higher than indicated in Table 7, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. The following examples describe the various distillation processes of the present invention.

EXAMPLES

Figure 4:
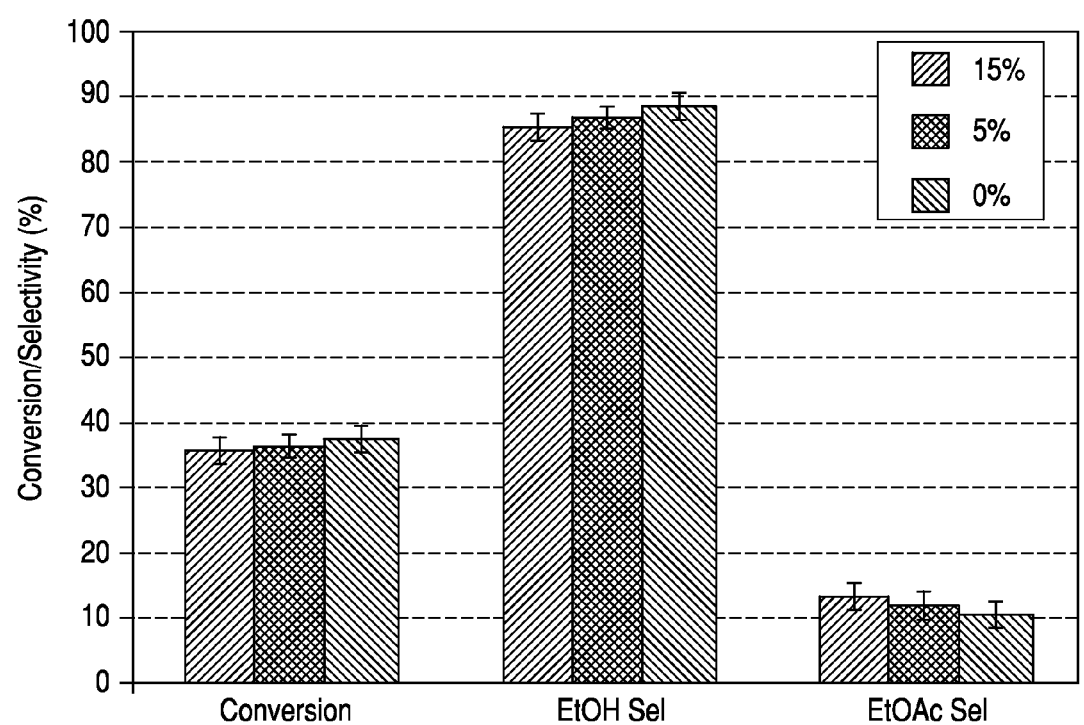
FIG. 4 is a chart of conversion and selectivity results from an exemplary process of the present invention.

Three acetic acid feed streams were prepared comprising 0 wt. % water, 5 wt. % water and 15 wt. % water. Each feed stream was vaporized along with hydrogen and fed to a reactor. The reactor was maintained at a temperature of 250° C. and a constant pressure of about 1,820 kPa. The catalyst comprised 1.6 wt. % platinum and 1 wt. % tin supported on ⅛ inch calcium silicate modified silica extrudates. The conversion and selectivity to ethanol and ethyl acetate are shown in FIG. 4. The slight changes in conversion and selectivity shown in FIG. 4 are too small to be statistically significant. As shown in FIG. 4, the error bar represents one standard deviation. Thus, the presence of water does not affect conversion and selectivity in the reactor.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
    (a) providing from a distillation column in a carbonylation process a purified acetic acid stream comprising from 0.5 wt. % to 25 wt. % water;
    (b) hydrogenating acetic acid of the purified acetic acid stream in the presence of a catalyst and under conditions effective to form a crude ethanol product comprising ethanol and water, wherein the purified acetic acid stream is fed directly from the carbonylation to the hydrogenation without removing substantially any water from the purified acetic acid stream; and
    (c) recovering ethanol from the crude ethanol product.

2. The process of claim 1, wherein purified acetic acid stream comprises water in an amount from 1 wt. % to 15 wt. %.

3. The process of claim 1, wherein the crude ethanol product comprises from 5 wt % to 70 wt % ethanol and from 5 wt % to 60 wt % water.

4. The process of claim 1, wherein the purified acetic acid stream further comprises halogens.

5. The process of claim 1, further comprising removing halogens from the purified acetic acid stream.

6. The process of claim 1, wherein the purified acetic acid stream comprises from 0.01 to 10 wt. % methyl acetate.

7. The process of claim 6, further comprising reducing the methyl acetate to form methanol, and ethanol.

8. The process of claim 1, wherein the distillation column comprises a light ends column of the carbonylation process.

9. The process of claim 6, wherein the purified acetic acid stream is provided as a sidestream from the light ends column.

10. The process of claim 1, further comprising:
    (d) separating at least a portion of the crude ethanol product to yield a distillate comprising ethanol, water, and ethyl acetate, and a residue comprising acetic acid and water.

11. The process of claim 10, wherein the residue comprises less than 90 wt. % acetic acid and from 30 to 100 wt. % water.

12. The process of claim 10, wherein the distillate comprises substantially no acetic acid.

13. The process of claim 10, wherein a weight ratio of water in the residue to water in the distillate is greater than 2:1.

14. The process of claim 10, wherein step (b) is conducted in a reaction zone and wherein at least a portion of the residue is recycled to the reaction zone.

15. The process of claim 1, wherein the acetic acid of the purified acetic acid stream is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

16. A process for producing ethanol, comprising the steps of:
    (a) withdrawing a purified acetic acid sidedraw from a light ends column of a carbonylation process;
    (b) hydrogenating acetic acid of the purified acetic acid sidedraw in the presence of a catalyst under conditions effective to form a crude ethanol product comprising ethanol and water, wherein the purified acetic acid sidedraw is fed directly to the hydrogenation without removing substantially any water from the purified acetic acid sidedraw; and
    (c) recovering ethanol from the crude ethanol product.

17. The process of claim 16, wherein purified acetic acid stream comprises water in an amount from 0.5 wt. % to 25 wt. % water.

18. The process of claim 16, wherein purified acetic acid stream comprises water in an amount from 1 wt. % to 15 wt. % water.

19. The process of claim 16, wherein the crude ethanol product comprises from 5 wt % to 70 wt % ethanol and from 5 wt % to 60 wt % water.

20. The process of claim 16, wherein the purified acetic acid sidedraw further comprises halogens.

21. The process of claim 20, further comprising removing halogens from the purified acetic acid stream.

22. The process of claim 16, wherein the purified acetic acid stream comprises from 0.01 to 10 wt. % methyl acetate.

23. The process of claim 22, further comprising reducing the methyl acetate to form methanol, and ethanol.

24. The process of claim 16, further comprising:
    (d) separating at least a portion of the crude ethanol product to yield a distillate comprising ethanol, water, and ethyl acetate, and a residue comprising acetic acid and water.

25. The process of claim 24, wherein the residue further comprises less than 90 wt. % acetic acid and from 30 to 100 wt. % water.

26. The process of claim 24, wherein the distillate comprises substantially no acetic acid.

27. The process of claim 24, wherein a weight ratio of water in the residue to water in the distillate is greater than 2:1.

28. A process for producing ethanol, comprising the steps of:
    (a) withdrawing a purified acetic acid sidedraw from a light ends column in a carbonylation process, wherein a location from which the sidedraw is withdrawn is based on a water content of the sidedraw;
    (b) hydrogenating acetic acid of the purified acetic acid stream in the presence of a catalyst under conditions effective to form a crude ethanol product comprising ethanol and water; and
    (c) recovering ethanol from the crude ethanol product.

29. The process of claim 28, wherein the water content of the sidedraw ranges from 0.5 wt % to 25 wt %.

* * * * *